(12) United States Patent
Chen et al.

(10) Patent No.: US 12,226,659 B2
(45) Date of Patent: Feb. 18, 2025

(54) NEUTRON CAPTURE THERAPY SYSTEM

(71) Applicant: NEUBORON THERAPY SYSTEM LTD., Fujian (CN)

(72) Inventors: Wei-Lin Chen, Jiangsu (CN); Tao Jiang, Jiangsu (CN); Fa-Zhi Yan, Jiangsu (CN)

(73) Assignee: NEUBORON THERAPY SYSTEM LTD., Fujian (CN)

( * ) Notice: Subject to any disclaimer, the term of this patent is extended or adjusted under 35 U.S.C. 154(b) by 0 days.

(21) Appl. No.: 18/657,438

(22) Filed: May 7, 2024

(65) Prior Publication Data
US 2024/0293682 A1 Sep. 5, 2024

Related U.S. Application Data

(63) Continuation of application No. 17/494,874, filed on Oct. 6, 2021, now Pat. No. 12,011,615, which is a continuation of application No. PCT/CN2020/079653, filed on Mar. 17, 2020.

(30) Foreign Application Priority Data

| Apr. 17, 2019 | (CN) | ......................... 201910308039.5 |
| Apr. 17, 2019 | (CN) | ......................... 201910308298.2 |
| Jul. 11, 2019 | (CN) | ......................... 201910623203.9 |

(51) Int. Cl.
*A61N 5/10* (2006.01)

(52) U.S. Cl.
CPC ...... *A61N 5/1065* (2013.01); *A61N 2005/109* (2013.01); *A61N 2005/1094* (2013.01)

(58) Field of Classification Search
None
See application file for complete search history.

(56) References Cited

U.S. PATENT DOCUMENTS

| 4,599,515 A | * | 7/1986 | Whittemore | ............. G21K 1/00 |
| | | | | 976/DIG. 428 |
| 7,475,651 B1 | | 1/2009 | Dunn | |

FOREIGN PATENT DOCUMENTS

| CN | 202802547 U | 3/2013 |
| CN | 104148897 A | 11/2014 |
| CN | 104771837 A | 7/2015 |
| CN | 107802968 A | 3/2018 |
| CN | 107998517 A | 5/2018 |
| CN | 108127344 A | 6/2018 |
| CN | 108136200 A | 6/2018 |

(Continued)

*Primary Examiner* — Edwin C Gunberg
(74) *Attorney, Agent, or Firm* — Lock Lord LLP; Tim Tingkang Xia, Esq.

(57) ABSTRACT

A neutron capture therapy system is provided, which may prevent a material of a beam shaping assembly from deformation and damaged, and improve the flux and quality of neutron sources. A boron neutron capture therapy system (100) includes a neutron generating device (10) and a beam shaping assembly (20). The neutron generating device (10) includes an accelerator (11) and a target (T). A charged particle beam (P) generated by acceleration of the accelerator (11) acts with the target (T) to generate neutrons. The neutrons form a neutron beam (N). The neutron beam (N) defines a main axis (X). The beam shaping assembly (20) includes a support part (21) and a main part (23) filled within the support part (21).

10 Claims, 6 Drawing Sheets

(56) References Cited

FOREIGN PATENT DOCUMENTS

| | | | |
|---|---|---|---|
| CN | 207856091 | U | 9/2018 |
| CN | 108926784 | A | 12/2018 |
| CN | 208335758 | U | 1/2019 |
| CN | 208372313 | U | 1/2019 |
| EP | 3369457 | A1 | 9/2018 |
| EP | 3456381 | A1 | 3/2019 |
| EP | 3456381 | B1 | 4/2020 |
| EP | 4082610 | A1 | 11/2022 |
| JP | S6274044 | A | 4/1987 |
| JP | H09188102 | A | 7/1997 |
| JP | 2006047115 | A | 2/2006 |
| JP | 2018161449 | A | 10/2018 |
| RU | 2540124 | C2 | 2/2015 |
| WO | 2017164408 | A1 | 9/2017 |
| WO | 2019037624 | A1 | 2/2019 |
| WO | 2019047697 | A1 | 3/2019 |

\* cited by examiner

NEUTRON CAPTURE THERAPY SYSTEM

CROSS-REFERENCE TO RELATED PATENT APPLICATION

This application is a continuation application of U.S. patent application Ser. No. 17/494,874, filed on Oct. 6, 2021, which itself is a continuation application of International Application No. PCT/CN2020/079653, filed on Mar. 17, 2020, which claims priority to Chinese Patent Application No. 201910308039.2, filed on Apr. 17, 2019; Chinese Patent Application No. 201910308298.5, filed on Apr. 17, 2019; and Chinese Patent Application No. 201910623203.9, filed on Jul. 11, 2019, the disclosures of which are hereby incorporated by reference.

FIELD

The present disclosure relates to a radiation irradiation system, and in particular to a neutron capture therapy system.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

As atomics moves ahead, such radiotherapy as Cobalt-60, linear accelerators and electron beams has been one of major means to cancer therapy. However, conventional photon or electron therapy has been undergone physical restrictions of radioactive rays; for example, many normal tissues on a beam path will be damaged as tumor cells are destroyed. On the other hand, sensitivity of tumor cells to the radioactive rays differs greatly, so in most cases, conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

Boron Neutron Capture Therapy (BNCT) takes advantage that the boron (B-10)-containing pharmaceuticals have high neutron capture cross section and produces $^4$He and $^7$Li heavy charged particles through $^{10}$B(n,$\alpha$)$^7$Li neutron capture and nuclear fission reaction. As illustrated in FIGS. 1 and 2, a schematic drawing of BNCT and a nuclear reaction formula of $^{10}$B (n,$\alpha$)$^7$Li neutron capture are shown, the two charged particles, with average energy at about 2.33 MeV, are of high linear energy transfer (LET) and short-range characteristics. LET and range of the alpha particle are 150 keV/micrometer and 8 micrometers respectively while those of the heavy charged particle $^7$Li are 175 keV/micrometer and 5 micrometers respectively, and the total range of the two particles approximately amounts to a cell size. Therefore, radiation damage to living organisms may be restricted at the cells' level. only the tumor cells will be destroyed on the premise of having no major normal tissue damage.

BNCT is also well known for binary cancer therapy, for its effectiveness depending on the concentration of the boronated pharmaceuticals and the number of the thermal neutrons at the tumor site. Thus, besides development of the boronated pharmaceuticals, improvement of flux and quality of the neutron source plays a significant role in BNCT researches.

Therefore, it is necessary to propose a new technical solution to resolve the foregoing problem.

SUMMARY

To improve the flux and quality of neutron sources, an aspect of the present invention provides a neutron capture therapy system, including a neutron generating device and a beam shaping assembly, where the neutron generating device includes an accelerator and a target, a charged particle beam generated by acceleration of the accelerator acts with the target to generate neutrons, the neutrons form a neutron beam, the neutron beam defines a main axis, the beam shaping assembly includes a support part and a main part filled within the support part, the main part includes a moderator, a reflector, and a radiation shield, the moderator is configured to moderate neutrons generated from the target to an epithermal neutron energy range, the reflector surrounds the moderator and directs deviating neutrons back to the main axis to enhance intensity of an epithermal neutron beam, and the radiation shield is provided to shield leaking neutrons and photons so as to reduce dose to normal tissues in a non-irradiation area. The support part is provided to prevent a material of the main part from deformation and damage, to avoid affecting the target change and beam quality.

Further, the support part includes an outer wall circumferentially closed around the main axis, the outer wall forms an accommodating portion surroundingly, the main part is disposed in the accommodating portion, the accommodating portion includes at least one accommodating unit, and each accommodating unit accommodates at least one of the moderator, the reflector, and the radiation shield.

Still further, the support part further includes a first side plate and a second side plate respectively disposed on two sides of the outer wall in a direction of the neutron beam and connected to the outer wall, at least one transverse plate disposed between the first side plate and the second side plate in the direction of the neutron beam, and at least one inner wall circumferentially closed around the main axis and extending between the first side plate and the second side plate or between the transverse plate and the first/second side plate or between the transverse plates, a hole for a transmitting tube of the accelerator to pass through is provided in the first side plate, a hole for forming a beam exit is provided in the second side plate, a plurality of accommodating units are formed between the outer wall, the inner wall, the transverse plate, the first side plate, and the second side plate, the radiation shield includes a neutron shield and a photon shield, and the at least one accommodating unit accommodates both the moderator/neutron shield and the reflector.

Preferably, the inner wall includes a first inner wall and a second inner wall, the transverse plate includes a first transverse plate, the first inner wall extends between the first side plate and the first transverse plate and is provided to mount the transmitting tube, and the second inner wall extends in the direction of the neutron beam from the first transverse plate and is provided to accommodate at least a part of the moderator.

Further, the moderator includes a basic portion and a supplementary portion, the accommodating unit includes a first accommodating unit and a second accommodating unit adjacent to each other, the basic portion is accommodated in the first accommodating unit, the basic portion is provided with a center hole at an end facing the first side plate, the center hole is provided to accommodate the transmitting tube and the target, the supplementary portion and at least a part of the reflector are accommodated in the second accommodating unit, the first accommodating unit is surrounded by the second inner wall, and a radial distance from the first inner wall to the main axis is less than a radial distance from the second inner wall to the main axis. The basic portion of the moderator surrounds the target, so that the neutrons generated by the target may be effectively moderated in all directions, so that the neutron flux and beam quality may be further improved.

Still further, the material of the basic portion is magnesium fluoride containing Li-6, the basic portion is also provided as a thermal neutron absorber, the supplementary portion includes a first supplementary unit and a second supplementary unit, the material of the first supplementary unit is an aluminum alloy, the material of the second supplementary unit is Teflon, the material of the reflector is lead, the reflector is also provided as the photon shield, the first supplementary unit and the second supplementary unit are integrally disposed as two tapered shapes adjacent to each other in opposite directions and divide the reflector in the second accommodating unit into two portions, the first supplementary unit and the second supplementary unit are sequentially disposed in the direction of the neutron beam, and an interface between the first supplementary unit and the second supplementary unit is perpendicular to the direction of the neutron beam. An aluminum alloy block and a Teflon block are respectively provided as the first supplementary unit and the second supplementary unit of the moderator, so that manufacturing costs of the moderator may be reduced, and the beam quality is not significantly affected. The first supplementary unit and the second supplementary unit are integrally disposed as two tapered shapes adjacent to each other in opposite directions, so that better beam quality and a better treatment effect may be achieved. Teflon also has a better fast neutron absorption effect, so that the content of fast neutrons in the beam may be reduced.

Still further, a lead shielding plate is further disposed between a magnesium fluoride block in the first accommodating unit and a positioning ring/stop ring, the basic portion and the shielding plate are sequentially disposed in the direction of the neutron beam, the positioning ring or the stop ring is made of a material with a short inherent half-life of the activated nucleus produced by an activation reaction, the material of the shielding plate is lead, and a thickness of the lead shielding plate in the direction of the neutron beam is less than or equal to 5 cm, so that neutrons passing through the moderator are not reflected, and lead may absorb gamma rays released from the moderator. The outer wall, at least one of the inner walls, and at least one of the transverse plates integrally form a main frame, the half-life of radioactive isotopes generated by materials of the main frame, the first side plate, and the second side plate after activation by neutrons is less than 7 days, and the material of the main frame, the first side plate, and the second side plate is an aluminum alloy, a titanium alloy, a lead-antimony alloy, cast aluminum, cobalt-free steel, carbon fiber, PEEK, or a high polymer. When the aluminum alloy is selected as the material of the main frame, the aluminum alloy has adequate mechanical properties and a short half-life of radioactive isotopes generated by the aluminum alloy after the aluminum alloy is activated by neutrons. When the lead-antimony alloy is selected as the material of the first side plate and the second side plate, lead may further shield against radiation, and the lead-antimony alloy has a relatively high strength.

Preferably, the accommodating unit includes a third accommodating unit, the neutron shield and at least a part of the reflector is accommodated in the third accommodating unit, the material of the neutron shield is PE, the material of the reflector is lead, the reflector is also provided as the photon shield, the reflector and the neutron shield in the third accommodating unit are sequentially disposed in the direction of the neutron beam, and an interface between the reflector and the neutron shield in the third accommodating unit is perpendicular to the direction of the neutron beam.

Preferably, the support part further includes radial partitions that circumferentially divide the accommodating unit into a plurality of subregions, the radial partitions are disposed between the first side plate and the second side plate or between the transverse plate and the first/second side plate or between the transverse plates, and extends from the outer wall to the inner wall or extends between the two inner walls.

Another aspect of the present invention provides a beam shaping assembly for a neutron capture therapy system. The neutron capture therapy system includes a neutron generating device, neutrons generated by the neutron generating device form a neutron beam, the beam shaping assembly may adjust beam quality of the neutron beam, the beam shaping assembly includes a support part and a main part filled within the support part, the support part forms at least one accommodating unit, and each accommodating unit accommodates at least a part of the main part. The support part is provided to prevent the material of the main part from deformation and damage, to avoid affecting the target change and beam quality.

A third aspect of the present invention provides a beam shaping assembly for a neutron capture therapy system. The neutron capture therapy system includes a neutron generating device, the neutron generating device includes an accelerator and a target, a charged particle beam generated by acceleration of the accelerator acts with the target to generate neutrons, the neutrons form a neutron beam, the neutron beam defines a main axis, the beam shaping assembly includes a moderator, a reflector, and a radiation shield, the moderator is configured to moderate neutrons generated by the neutron generating device to an epithermal neutron energy range, the reflector surrounds the moderator and directs deviating neutrons back to the main axis to enhance intensity of an epithermal neutron beam, the radiation shield is provided to shield leaking neutrons and photons so as to reduce dose to normal tissues in a non-irradiation area, the moderator includes a basic portion and a supplementary portion surrounding the basic portion, the beam shaping assembly further includes a support part for supporting the beam shaping assembly, the support part includes a wall around the main axis, and the basic portion and the supplementary portion are made of different materials and are separated by the wall. The support part is provided to prevent a material of the main part of the beam shaping assembly from deformation and damage, to avoid affecting the target change and beam quality. An easily available material is selected for the supplementary portion, so that manufacturing costs of the moderator may be reduced, particular neutron moderation is implemented, and the beam quality is not significantly affected.

Preferably, the wall includes a first wall, a second wall, and a transverse plate connecting the first wall and the second wall that are sequentially disposed in the direction of the neutron beam and are circumferentially closed around the direction of the neutron beam, the transverse plate extends perpendicular to the direction of the neutron beam, the first wall is provided to mount a transmitting tube of the accelerator, the second wall forms an accommodating cavity for the basic portion of the moderator, the material of the basic portion includes at least one of $D_2O$, Al, $AlF_3$, $MgF_2$, $CaF_2$, LiF, $Li_2CO_3$, or $Al_2O_3$, which has a large cross section for interacting with fast neutrons and has a small cross section for interacting with epithermal neutrons, thereby implementing adequate moderation; and the basic portion contains Li-6, and the basic portion is also provided as a thermal neutron absorber. Further, the basic portion includes a first end surface and a second end surface that are approximately perpendicular to the direction of the neutron beam, the first end surface and the second end surface are sequentially disposed in the direction of the neutron beam, the first end surface is provided with a center hole, the center hole is provided to accommodate the transmitting tube and the target, a radial distance from the first wall to the main axis is less than a radial distance from the second wall to the main axis, and the basic portion of the moderator surrounds the target, so that the neutrons generated by the target may be effectively moderated in all directions, so that the neutron flux and beam quality may be further improved. A shielding plate is disposed adjacent to the second end surface, the shielding plate is a lead plate, and lead may absorb gamma rays released from the moderator. A thickness of the shielding plate in the direction of the neutron beam is less than or equal to 5 cm, so that neutrons passing through the moderator are not reflected.

Further preferably, the support part further includes radial partitions that divide the supplementary portion into at least two submodules circumferentially around the main axis, a plane where the radial partition is located extends through the main axis, and the at least two submodules are separated by the radial partition.

Further preferably, the supplementary portion includes a first supplementary unit and a second supplementary unit adjacent to each other, the basic portion, the first supplementary unit, and the second supplementary unit are made of three different materials, the basic portion is cylindrical, and the first supplementary unit and the second supplementary unit are integrally disposed as a shape including at least one tapered shape, so that better beam quality and a better treatment effect may be achieved.

Further, a material of the first supplementary unit includes at least one of Zn, Mg, Al, Pb, Ti, La, Zr, Bi, Si, and C, and a material of the second supplementary unit is Teflon or graphite. The first supplementary unit and the second supplementary unit are sequentially disposed in the direction of the neutron beam, and the first supplementary unit and the second supplementary unit are integrally disposed as two tapered shapes adjacent to each other in opposite directions. An easily available material is selected for the first supplementary unit of the moderator, so that manufacturing costs of the moderator may be reduced, particular neutron moderation is implemented, and the beam quality is not significantly affected. A material with a better fast neutron absorption effect than the material of the first supplementary unit is selected for the second supplementary unit, so that the content of fast neutrons in the beam may be reduced.

Further, the first supplementary unit is disposed as two tapered shapes adjacent to each other in opposite directions, the first supplementary unit includes a first tapered section and a second tapered section that are sequentially disposed in the direction of the neutron beam, a radial size of an outer contour of the first tapered section gradually increases in the direction of the neutron beam as a whole, the second tapered section is connected to the first tapered section at a position where the radial size of the outer contour of the first tapered section is maximum, a radial size of an outer contour of the second tapered section gradually decreases in the direction of the neutron beam as a whole, the second supplementary unit is adjacent to the second tapered section at a position where the radial size of the outer contour of the second tapered section is minimum, and a radial size of an outer contour of the second supplementary unit gradually decreases in the direction of the neutron beam as a whole.

Still further, cross section contours of the first supplementary unit and the second supplementary unit in a plane where the main axis is located are irregular quadrilaterals or polygons, the first supplementary unit includes a first side in contact with the reflector at the first tapered section, a second side in contact with the reflector and a third side in contact with the second supplementary unit at the second tapered section, and a fourth side in contact with the wall at both the first tapered section and the second tapered section, the second supplementary unit includes a fifth side in contact with the first supplementary unit, a sixth side in contact with the reflector, and a seventh side in contact with the wall, the third side and the fifth side are adjacent and are provided as an interface between the first supplementary unit and the second supplementary unit, and the interface is perpendicular to the direction of the neutron beam.

A fourth aspect of the present invention provides a beam shaping assembly for a neutron capture therapy system. The neutron capture therapy system includes a neutron generating device, neutrons generated by the neutron generating device form a neutron beam, the neutron beam defines a main axis, the beam shaping assembly may adjust the beam quality of the neutron beam, the beam shaping assembly includes a support part and a main part filled within the support part, the support part includes a support frame, the support frame is formed by heating a blank material with a heating equipment, and then performing forging into a cylinder with a forging equipment, the cylinder is processed with a machining equipment after rough machining and heat treatment. The support part is provided to prevent the material of the main part from deformation and damage, to avoid affecting the target change and beam quality. The support frame requires a few forging procedures and a smaller number of times of heating, has a homogenized structure and adequate forging performance, and saves raw materials. The blank material is heated before forging, so that deformation resistance may be reduced and plasticity may be improved. After rough machining is performed on the forged cylinder, the overall material properties of the support frame after heat treatment may be ensured.

Further, a material of the support frame is an aluminum alloy, and a mass percentage of Cu in the aluminum alloy is ≤7%, which may meet the requirement of a short half-life of radioactive isotopes generated by the support frame after activation by neutrons. For the support frame, tensile strength of the material is ≥150 MPa, and yield strength of the material is ≥100 MPa, so that the support frame may support the main part of the beam shaping assembly. The aluminum alloy is a wrought aluminum alloy. The forging equipment is free forging equipment, and the free forging equipment includes upsetting and drawing equipment. The structure and properties of the aluminum alloy are changed through free forging by using a plastic forming method, and raw materials may be further saved.

Further, the heating equipment is a radiant resistance heating furnace, there is circulating air in the furnace to keep the temperature accurate and uniform, the furnace temperature deviation is ±10° C., the maximum initial forging temperature is 520° C., the final forging temperature is 450° C., and the allowable limit temperature is 530° C. The heating time may be determined according to dissolution of a strengthening phase and structure homogenization. In this state, adequate plasticity may be obtained, and the forging performance of an aluminum alloy may be improved.

Further, the main part includes a moderator, a reflector, and a radiation shield, the moderator is configured to moderate neutrons generated by the neutron generating device to an epithermal neutron energy range, the reflector surrounds the moderator and directs deviating neutrons back to the main axis to enhance intensity of an epithermal neutron beam, the radiation shield is provided to shield leaking neutrons and photons so as to reduce dose to normal tissues in a non-irradiation area, the support frame forms at least one accommodating unit, and each accommodating unit accommodates at least a part of the main part.

Still further, the accommodating unit includes a first accommodating unit accommodating at least a part of the moderator, the first accommodating unit is located at the center of the support frame in the radial direction, and the rough machining is drilling holes in regions of the cylinder corresponding to the first accommodating unit. When heat treatment is directly performed on the cylinder, it is difficult to ensure the performance of a material at the center of the cylinder. Therefore, a hole is drilled at a center position (that is, the regions of the cylinder corresponding to the first accommodating unit) of the forged cylinder through rough machining, and deep heat treatment is then performed, so that it may be ensured that the support frame is close to the center position (to form a main frame portion of the first accommodating unit) and ensure the overall material properties after the heat treatment. In addition, the first accommodating unit accommodates the moderator, so that the support for the moderator may be ensured, and the moderator is prevented from deformation and damage, to avoid affecting the target change and beam quality.

Still further, the accommodating unit includes a second accommodating unit accommodating at least one of the moderator, the reflector, and the radiation shield, the support frame includes an outer wall circumferentially closed around the main axis and at least one inner wall, the second accommodating unit is formed between the outer wall and the inner wall or between the inner walls, and the rough machining further includes preliminary machining of regions of the cylinder corresponding to the second accommodating unit. It may be understood that the rough machining may not be performed on the regions of the cylinder corresponding to the second accommodating unit to prevent the regions from easy deformation caused by a thin thickness during heat treatment after the rough machining.

Further, the heat treatment includes solution treatment and aging treatment, aluminum after solution treatment is kept at a particular temperature for a particular time, and a supersaturated solid solution decomposes to cause the strength and hardness of the alloy to increase greatly.

A fifth aspect of the present invention provides a method for treating a support frame of a beam shaping assembly, including:
heating: heating a blank material that meets the material requirements of the support frame at a particular temperature and for a particular time;
forging: forging the heated blank material into a cylinder;
rough machining: drilling a hole is at a center position of the cylinder obtained by forging;
heat treatment: performing heat treatment on a forged body obtained after the rough machining; and
machining: machining the forged body after the heat treatment to obtain the support frame with a final required shape and size.

The support frame is provided to prevent the material of the main part from deformation and damage, to avoid affecting the target change and beam quality. The support frame requires a few forging procedures and a smaller number of times of heating, has a homogenized structure and adequate forging performance, and saves raw materials.

The blank material is heated before forging, so that deformation resistance may be reduced and plasticity may be improved. A hole is drilled at the center position of the forged cylinder, and the heat treatment is then performed, so that it may be ensured that the support frame is close to the center position and ensure the overall material properties after the heat treatment.

Further, before the step of the heating, the blank material is detected to meet the raw material requirements of the support frame; before the step of the forging, the blank material is treated to meet the processing requirements of the forging equipment; the forging is free forging, including upsetting and drawing, under the condition that the forging temperature is not less than a specified temperature, static forging is repeated according to processes of the foregoing two methods to obtain precise grains in the structure, and the forging equipment has the precision of forging a blank; the heat treatment includes solution treatment and aging treatment, aluminum after solution treatment is kept at a particular temperature for a particular time, and a supersaturated solid solution decomposes to cause the strength and hardness of the alloy to increase greatly; and after the heat treatment, physical and chemical testing and inspection are performed, including size testing, element testing, mechanical property testing, and non-destructive ultrasonic flaw detection testing.

In the present invention, the beam shaping assembly of the neutron capture therapy system may prevent the material of the beam shaping assembly from deformation and damaged, and improve the flux and quality of neutron sources.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Embodiments of the present invention are further described below in detail with reference to the accompanying drawings, to enable a person skilled in the art to implement the present invention with reference to the text of the specification.

Figure 3:
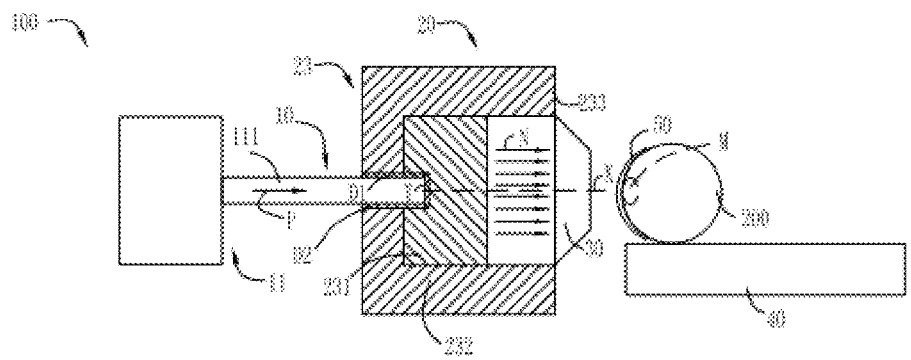
FIG. 3 is a schematic diagram of a neutron capture therapy system according to an embodiment of the present disclosure.

As shown in FIG. 3, a neutron capture therapy system in this embodiment is preferably a boron neutron capture therapy system 100, which includes a neutron generating device 10, a beam shaping assembly 20, a collimator 30, and a treatment table 40. The neutron generating device 10 includes an accelerator 11 and a target T, and the accelerator 11 accelerates charged particles (such as protons, deuterons, etc.) to generate a charged particle beam P such as a proton beam, and the charged particle beam P irradiates the target T and interacts with the target T to generate neutrons which form a neutron beam N, the neutron beam define a main axis X, and the target T is a metal target. The neutron beam N direction described below with reference to the accompanying drawings does not represent the actual neutron motion direction, but the overall motion trend direction of the neutron beam N. Suitable nuclear reactions are always determined according to such characteristics as desired neutron yield and energy, available accelerated charged particle energy and current and materialization of the metal target, among which the most discussed two are $^7Li$ (p, n) $^7Be$ and $^9Be$ (p, n) $^9B$ and both are endothermic reaction. Their energy thresholds are 1.881 MeV and 2.055 MeV respectively. Epithermal neutrons at a keV energy level are considered ideal neutron sources for BNCT. Theoretically, bombardment with lithium target using protons with energy slightly higher than the thresholds may produce neutrons relatively low in energy, so the neutrons may be used clinically without many moderations. However, Li (lithium) and Be (beryllium) and protons of threshold energy exhibit not high action cross section. In order to produce sufficient neutron fluxes, high-energy protons are usually selected to trigger the nuclear reactions. The target, considered perfect, is supposed to have the advantages of high neutron yield, a produced neutron energy distribution near the epithermal neutron energy range (see details thereinafter), little strong-penetration radiation, safety, low cost, easy accessibility, high temperature resistance etc. But in reality, no nuclear reactions may satisfy all requests. However, well known by those skilled in the art, the target materials may be made of other metals besides Li or Be, for example, tantalum (Ta) or tungsten (W) or their alloys. The accelerator 11 may be a linear accelerator, a cyclotron, a synchrotron, a synchrocyclotron.

Only mixed radiation fields are produced from BNCT neutron sources, that is, beams include neutrons and photons having energies from low to high. As for BNCT in the depth of tumors, except the epithermal neutrons, the more the residual quantity of radiation ray is, the higher the proportion of nonselective dose deposition in the normal tissue is. Therefore, radiation causing unnecessary dose should be lowered down as much as possible. Besides air beam quality factors, dose is calculated using a human head tissue prosthesis in order to understand dose distribution of the neutrons in the human body. The prosthesis beam quality factors are later used as design reference to the neutron beams, which is elaborated hereinafter.

The International Atomic Energy Agency (IAEA) has given five suggestions on the air beam quality factors for the clinical BNCT neutron sources. The suggestions may be used for differentiating the neutron sources and as reference for selecting neutron production pathways and designing the beam shaping assembly, and are shown as follows:

Epithermal neutron flux>1×109 n/cm²s
Fast neutron contamination<2×10$^{-13}$ Gy-cm²/n
Photon contamination<2×10$^{-13}$ Gy-cm²/n
Thermal to epithermal neutron flux ratio<0.05
1Epithermal neutron current to flux ratio>0.7
Note: the epithermal neutron energy range is between 0.5 eV and 40 keV, the thermal neutron energy range is lower than 0.5 eV, and the fast neutron energy range is higher than 40 keV.

1. Epithermal Neutron Flux

The epithermal neutron flux and the concentration of the boronated pharmaceuticals at the tumor site codetermine clinical therapy time. If the boronated pharmaceuticals at the tumor site are high enough in concentration, the epithermal neutron flux may be reduced. On the contrary, if the concentration of the boronated pharmaceuticals in the tumors is at a low level, it is required that the epithermal neutrons in the high epithermal neutron flux should provide enough doses to the tumors. The given standard on the epithermal neutron flux from IAEA is more than $10^9$ epithermal neutrons per square centimeter per second. In this flux of neutron beams, therapy time may be approximately controlled shorter than an hour with the boronated pharmaceuticals. Thus, except that patients are well positioned and feel more comfortable in shorter therapy time, and limited residence time of the boronated pharmaceuticals in the tumors may be effectively utilized.

2. Fast Neutron Contamination

Unnecessary dose on the normal tissue produced by fast neutrons is considered as contamination. The dose exhibits positive correlation to neutron energy, hence, the quantity of the fast neutrons in the neutron beams should be reduced to the greatest extent. Dose of the fast neutrons per unit epithermal neutron flux is defined as the fast neutron contamination, and according to IAEA, it is supposed to be less than 2*10$^{-13}$ Gy-cm²/n.

3. Photon Contamination (Gamma-Ray Contamination)

Gamma-ray long-range penetration radiation will selectively result in dose deposit of all tissues in beam paths, so that lowering the quantity of gamma-ray is also the exclusive requirement in neutron beam design. Gamma-ray dose accompanied per unit epithermal neutron flux is defined as gamma-ray contamination which is suggested being less than $2*10^{-13}$ Gy-cm$^2$/n according to IAEA.

4. Thermal to Epithermal Neutron Flux Ratio

The thermal neutrons are so fast in rate of decay and poor in penetration that they leave most of energy in skin tissue after entering the body. Except for skin tumors like melanocytoma, the thermal neutrons serve as neutron sources of BNCT, in other cases like brain tumors, the quantity of the thermal neutrons has to be lowered. The thermal to epithermal neutron flux ratio is recommended at lower than 0.05 in accordance with IAEA.

5. Epithermal Neutron Current to Flux Ratio

The epithermal neutron current to flux ratio stands for beam direction, the higher the ratio is, the better the forward direction of the neutron beams is, and the neutron beams in the better forward direction may reduce dose surrounding the normal tissue resulted from neutron scattering. In addition, treatable depth as well as positioning posture is improved. The epithermal neutron current to flux ratio is better of larger than 0.7 according to IAEA.

The prosthesis beam quality factors are deduced by virtue of the dose distribution in the tissue obtained by the prosthesis according to a dose-depth curve of the normal tissue and the tumors. The three parameters as follows may be used for comparing different neutron beam therapy effects.

1. Advantage Depth

Tumor dose is equal to the depth of the maximum dose of the normal tissue. Dose of the tumor cells at a position behind the depth is less than the maximum dose of the normal tissue, that is, boron neutron capture loses its advantages. The advantage depth indicates penetrability of neutron beams. Calculated in cm, the larger the advantage depth is, the larger the treatable tumor depth is.

2. Advantage Depth Dose Rate

The advantage depth dose rate is the tumor dose rate of the advantage depth and also equal to the maximum dose rate of the normal tissue. It may have effects on length of the therapy time as the total dose on the normal tissue is a factor capable of influencing the total dose given to the tumors. The higher it is, the shorter the irradiation time for giving a certain dose on the tumors is, calculated by cGy/mA-min.

3. Advantage Ratio

The average dose ratio received by the tumors and the normal tissue from the brain surface to the advantage depth is referred to as an advantage ratio. The average ratio may be calculated using dose-depth curvilinear integral. The higher the advantage ratio is, the better the therapy effect of the neutron beams is.

To provide comparison reference to design of the beam shaping assembly, we also provide the following parameters for evaluating expression advantages and disadvantages of the neutron beams in the embodiments of the present disclosure except the air beam quality factors of IAEA and the abovementioned parameters.

1. Irradiation time≤30 min (proton current for accelerator is 10 mA)
2. 30.0 RBE-Gy treatable depth≥7 cm
3. The maximum tumor dose≥60.0 RBE-Gy
4. The maximum dose of normal brain tissue ≤12.5 RBE-Gy
5. The maximum skin dose≤11.0 RBE-Gy Note: RBE stands for relative biological effectiveness. Since photons and neutrons express different biological effectiveness, the dose above should be multiplied with RBE of different tissues to obtain equivalent dose.

Figure 1:
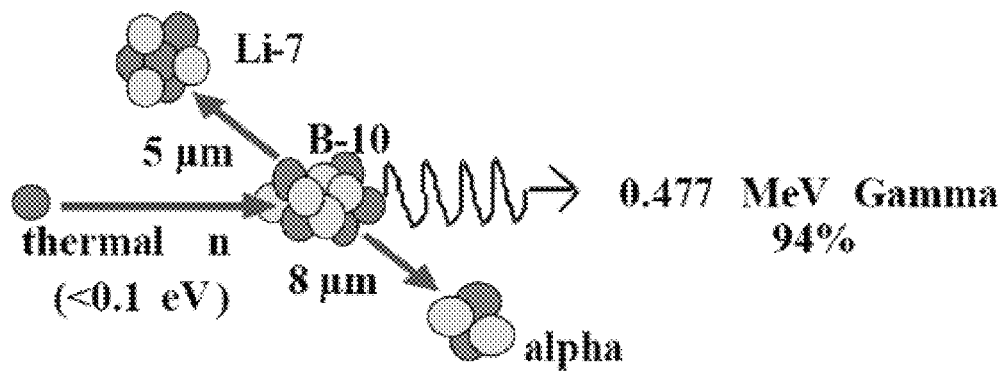
FIG. 1 is a schematic diagram of a boron neutron capture reaction.
Figure 2:
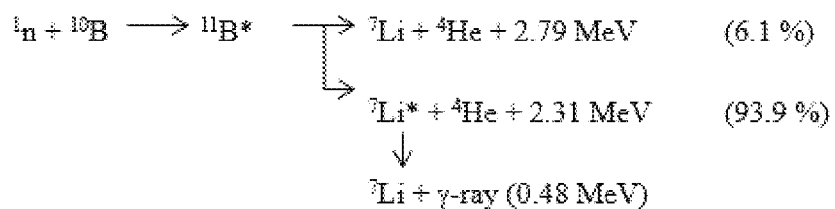
FIG. 2 shows a nuclear reaction equation of $^{10}B(n,\alpha)^7Li$ neutron capture.

The neutron beam N generated by the neutron generating device 10 sequentially passes through the beam shaping assembly 20 and the collimator 30 and then irradiates to a patient 200 on the treatment table 40. The beam shaping assembly 20 is capable of adjusting the beam quality of the neutron beam N generated by the neutron generating device 10, and the collimator 30 is provided to concentrate the neutron beam N, so that the neutron beam N has higher targeting during the treatment process. The beam shaping assembly 20 further includes a support part 21 (not shown in FIG. 1, detailed below) and a main part 23 filled within the support part 21, the support part 21 forms at least one accommodating unit C1-C10, each containing at least a portion of the main part 23. The support part may prevent the deformation and damage of the material of the main part and affect the target replacing and quality of the beam. The main part 23 includes a moderator 231, a reflector 232, a radiation shield 233. The neutrons generated by the neutron generating device 10 have a wide spectrum of energy, and in addition to epithermal neutrons to meet treatment needs, it is desirable to reduce other types of neutrons and photons as much as possible to avoid injury to operators or patients. Therefore, the neutrons coming out of the neutron generating device 10 need to pass through the moderator 231 to adjust the energy of fast neutrons therein to the epithermal neutron energy region. The moderator 231 is made of a material having a cross section for principally acting with fast neutrons but hardly acting with epithermal neutrons, such as includes at least one of $D_2O$, $AlF_3$, Fluental, $CaF_2$, $Li_2CO_3$, $MgF_2$ and $Al_2O_3$. The reflector 232 surrounds the moderator 231, and reflects the neutrons diffused through the moderator 231 back to the neutron beam N to improve the utilization of the neutrons, and is made of a material having high neutron reflection ability, such as includes at least one of Pb and Ni. The radiation shield 233 is provided to shield against leaking neutrons and photons so as to reduce dose of a normal tissue not exposed to irradiation. The material of the radiation shield 233 includes at least one of a photon shielding material and a neutron shielding material, such as a photon shielding material lead (Pb) and a neutron shielding material polyethylene (PE). It should be appreciated that the main part may have other configurations as long as the epithermal neutron beam required for treatment may be obtained.

The target T is disposed between the accelerator 11 and the beam shaping assembly 20, and the accelerator 11 has a transmitting tube 111 that transmits the charged particle beam P. In this embodiment, the transmitting tube 111 penetrates into the beam shaping assembly 20 in the direction of the charged particle beam P, and sequentially passes through the moderator 231 and the reflector 232. The target T is arranged into the moderator 231 and located at the end of the transmitting tube 111 to obtain a better neutron beam quality. In this embodiment, first and second cooling pipes D1 and D2 are disposed between the transmitting tube 111 and the moderator 231, and between the transmitting tube 111 and the reflector 232, and one end of the first and second cooling pipes D1, D2 is respectively connected to the cooling inlet IN (not shown in Figs) and the cooling outlet OUT (not shown in Figs) of the target T, and the other ends are connected to an external cooling source (not shown in Figs). It should be understood that the first and second cooling tubes may also be disposed into the beam shaping assembly in other ways, and may also be omitted when the target is placed outside the beam shaping assembly.

Figure 4:
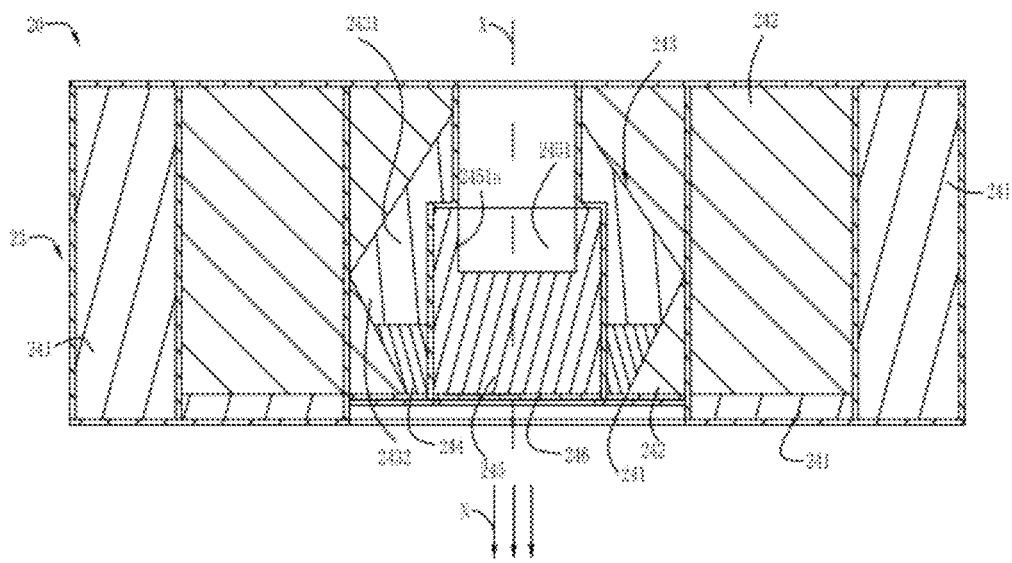
FIG. 4 is a schematic diagram of a beam shaping assembly of a neutron capture therapy system according to an embodiment of the present disclosure.
Figure 5:
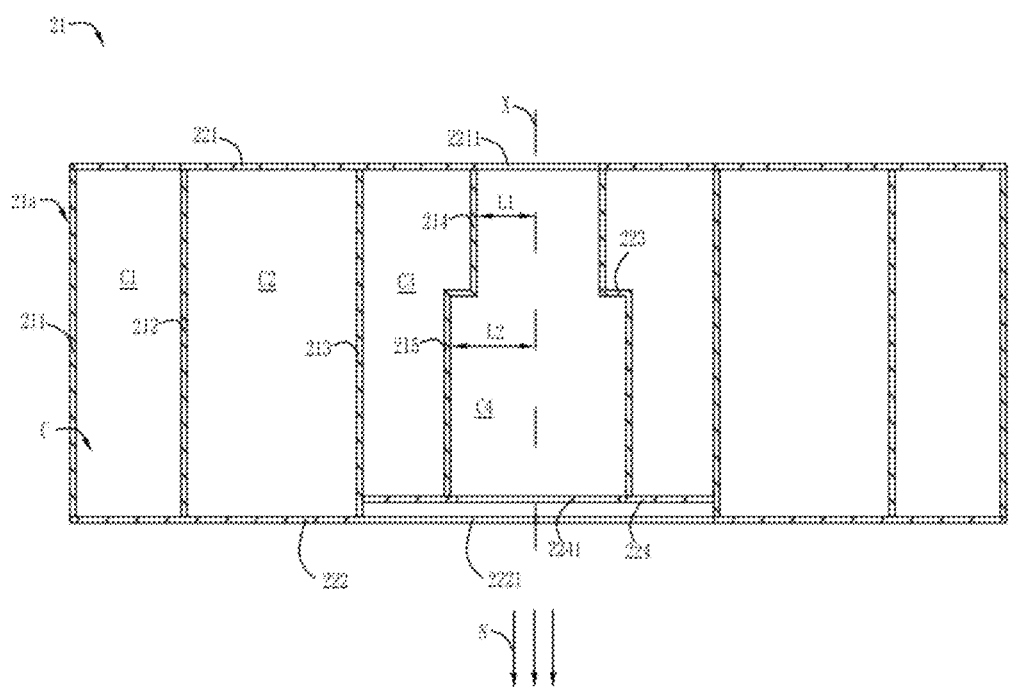
FIG. 5 is a schematic diagram of a support part in FIG. 4.

Referring to FIG. 4 and FIG. 5, the support part 21 includes an outer wall 211 circumferentially closed around the main axis X and a first side plate 221 and a second side plate 222 respectively disposed on two sides of the outer wall 211 in a direction of the neutron beam N and connected to the outer wall 211, a hole 2211 for a transmitting tube 111 to pass through is provided in the first side plate 221, a hole 2221 for forming a beam exit is provided in the second side plate 222, an accommodating portion C is formed between the outer wall 211, the first side plate 221, and the second side plate 222, and the main part 23 is disposed in the accommodating portion C. The accommodating portion C includes at least one accommodating unit C1-C4 (described in detail below), each accommodating unit C1-C4 accommodates at least one of the moderator 231, the reflector 232, and the radiation shield 233, the at least one accommodating unit C1-C4 accommodates at least two of the moderator, the reflector, and the radiation shield, or accommodates at least two different materials. It may be understood that the first side plate and the second side plate may not be disposed, and the outer wall surrounds the accommodating portion.

The support part 21 further includes at least one inner wall circumferentially closed around the main axis X and extending between the first side plate 221 and the second side plate 222. In this embodiment, a first inner wall 212 and a second inner wall 213 are disposed inward in a radial direction, and the radial direction is defined as a direction perpendicular to the main axis X. The support part 21 further includes a first transverse plate 223 disposed between the first side plate 221 and the second side plate 222 in the direction of the neutron beam N, a third inner wall 214 circumferentially closed around the main axis X and extending between the first transverse plate 223 and the first side plate 221, and a fourth inner wall 215 circumferentially closed around the main axis X and extending from the first transverse plate 223 to the second side plate 222. The third inner wall 214 is closer to the main axis X in the radial direction than the second inner wall 213, the fourth inner wall 215 is located radially between the second inner wall 213 and the third inner wall 214, and the first transverse plate 223 extends between the third inner wall 214 and the fourth inner wall 215. An inner surface of the third inner wall 214 is on the same surface as a side wall of the hole 2211 in the first side plate 221, and the third inner wall 214 forms a mounting portion for the transmitting tube 111, the first cooling pipe D1, the second cooling pipe D2, and the like. A second transverse plate 224 is disposed between the fourth inner wall 215 and the second side plate 222 and is adjacent to the fourth inner wall 215 in the direction of the neutron beam N, the second transverse plate 224 extends radially inward from the second inner wall 213, a hole 2241 for the neutron beam N to pass through is provided in the second transverse plate 224, and an inner wall of the hole 2241 is closer to the main axis X than an inner side of the fourth inner wall 215. It may be understood that the second transverse plate may not be disposed, the first transverse plate may extend to the outer wall or another inner wall, and a plurality of transverse plates may be alternatively disposed between the outer wall and the inner wall, and between the inner walls.

In this embodiment, the entire beam shaping assembly is cylindrical, cross sections of the outer wall and the inner wall in a direction perpendicular to the main axis X are rings around the main axis X and extend parallel to the main axis X, and the side plate and the transverse plate are flat plates extending perpendicular to the main axis X. It may be understood that, there may be alternatively another arrangement. For example, the extension direction is inclined to the main axis, and an outer contour of the outer wall in a direction perpendicular to the main axis may be alternatively square, rectangular, or polygonal, which is convenient for transportation and mounting. A first accommodating unit C1 is formed between the outer wall 211, the first inner wall 212, the first side plate 221, and the second side plate 222. A second accommodating unit C2 is formed between the first inner wall 212, the second inner wall 213, the first side plate 221, and the second side plate 222. A third accommodating unit C3 is formed between the second inner wall 213, the third inner wall 214, the fourth inner wall 215, the first side plate 221, the first transverse plate 223, and the second transverse plate 224.

In this embodiment, a PE block 241 of a corresponding shape is disposed in the first accommodating unit C1, a lead block 242 and the PE block 241 are sequentially disposed in the second accommodating unit C2 in the direction of the neutron beam N, the volume ratio of the lead block to the PE block is less than or equal to 10, and an interface between the lead block and the PE block is perpendicular to the direction of the neutron beam N. It may be understood that there may be alternatively other ratios or other distributions. In this embodiment, the radiation shield 233 includes a neutron shield and a photon shield, the PE block 241 is provided as the neutron shield, and the lead block 242 is provided as the reflector 232 and the photon shield.

In this embodiment, the lead block 242, an aluminum alloy block 243, a Teflon block 244, and the PE block 241 are disposed in the third accommodating unit C3, the aluminum alloy block 243 and the Teflon block 244 are integrally disposed as a shape including at least one tapered shape, the PE block 241 is disposed adjacent to the second transverse plate 224, the lead block 242 fills the remaining region, and the aluminum alloy block 243 and the Teflon block 244 divide the lead block 242 in the third accommodating unit C3 into two portions. The aluminum alloy block 243 and the Teflon block 244 are respectively provided as the first supplementary unit and the second supplementary unit of the moderator 231, so that manufacturing costs of the moderator may be reduced, and the beam quality is not significantly affected. The first supplementary unit and the second supplementary unit are disposed as a shape including at least one tapered shape, so that better beam quality and a better treatment effect may be achieved. The Teflon block 244 also has a better fast neutron absorption effect, so that the content of fast neutrons in the beam may be reduced. The lead block 242 is provided as the reflector 232 and the photon shield. The PE block 241 is provided as the neutron shield. It may be understood that the PE block may not be disposed.

Figure 6:
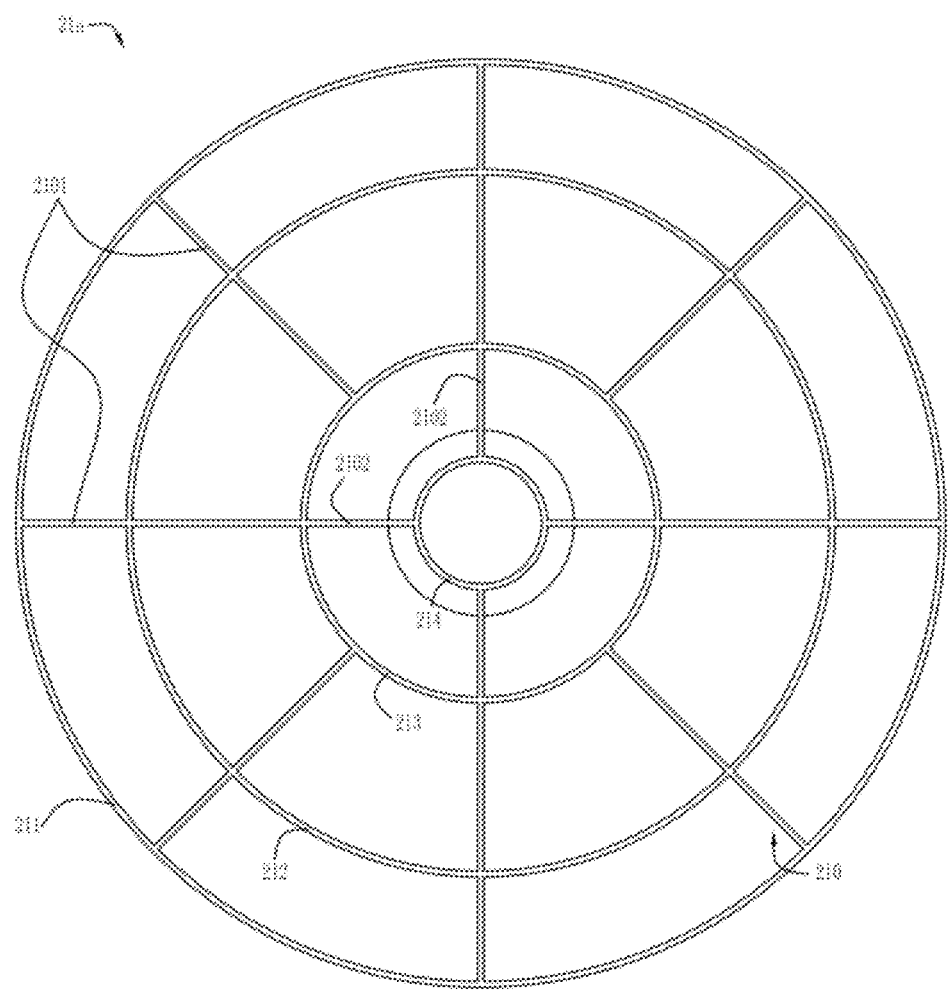
FIG. 6 is a schematic exploded view of a moderator in FIG. 4.

Referring to FIG. 6, in this embodiment, the aluminum alloy block 243 and the Teflon block 244 are sequentially disposed in the direction of the neutron beam N, the aluminum alloy block 243 and the Teflon block 244 are disposed as two tapered shapes adjacent to each other in opposite directions, the aluminum alloy block 243 is also disposed as two tapered shapes adjacent to each other in opposite directions, the aluminum alloy block 243 includes a first tapered section 2431 and a second tapered section 2432 that are sequentially disposed in the direction of the neutron beam N, the radial size of an outer contour of the first tapered section 2431 gradually increases in the direction of the neutron beam N as a whole, the second tapered section 2432 is connected to the first tapered section 2431 at a position where the radial size of the outer contour of the first tapered section 2431 is maximum, and the radial size of an outer contour of the second tapered section 2432 gradually decreases in the direction of the neutron beam N as a whole. The Teflon block 244 is adjacent to the second tapered section 2432 at a position where the radial size of the outer contour of the second tapered section 2432 is minimum, the radial size of an outer contour of the Teflon block 244 gradually decreases in the direction of the neutron beam N as a whole, and the Teflon block is in contact with the PE block 241 at a position where the radial size of the outer contour is maximum. Cross section contours of the aluminum alloy block 243 and the Teflon block 244 in a plane where the main axis X is located are irregular quadrilaterals or polygons. The aluminum alloy block 243 has a first side A1 in contact with the lead block 242 in the first tapered section 2431, a second side A2 in contact with the lead block 242 and a third side A3 in contact with the Teflon block 244 in the second tapered section 2432, and a fourth side A4 in contact with the third inner wall 214, the fourth inner wall 215, and the first transverse plate 223 in the first tapered section and the second tapered section. In this embodiment, the fourth side A4 is a stepped surface. The Teflon block 244 has a fifth side A5 in contact with the aluminum alloy block 243, a sixth side A6 in contact with the lead block 242, a seventh side A7 in contact with the fourth inner wall 215, and an eighth side A8 in contact with the PE block 241. The third side A3 and the fifth side A5 are adjacent to each other and are provided as an interface between the aluminum alloy block 243 and the Teflon block 244. In this embodiment, the interface is perpendicular to the direction of the neutron beam N. In this embodiment, the volume ratio of the aluminum alloy block 243 to the Teflon block 244 is 5 to 20. It may be understood that there may be alternatively other ratios or other distributions according to the neutron beam required for treatment, for example, different irradiation depths.

A region from the first transverse plate 223 to the second transverse plate 224 in the direction of the neutron beam N and surrounded by the fourth inner wall 215 forms a fourth accommodating unit C4, and the fourth accommodating unit C4 is adjacent to the third accommodating unit C3 in the radial direction. In this embodiment, a magnesium fluoride block 245 is disposed in the fourth accommodating unit C4 as the basic portion of the moderator 231, and the magnesium fluoride block 245 contains Li-6 and is also provided as a thermal neutron absorber, so that the first supplementary unit and the second supplementary unit of the moderator disposed in the third accommodating unit C3 surround the basic portion of the moderator disposed in the fourth accommodating unit C4. The entire magnesium fluoride block 245 is cylindrical, including a first end surface A9 and a second end surface A10 that are approximately perpendicular to the direction of the neutron beam N. The first end surface A9 and the second end surface A10 are sequentially disposed in the direction of the neutron beam. The first end surface A9 faces the first side plate 221 and is provided with a center hole 2451. The center hole 2451 is provided to accommodate the transmitting tube 111, the first cooling pipe D1, the second cooling pipe D2, and the target T. The center hole 2451 is a cylindrical hole. A side wall 2451a of the center hole is on the same surface as an inner surface of the third inner wall. A radial distance L1 from the third inner wall 214 to the main axis X is less than a radial distance L2 from the fourth inner wall 215 to the main axis X, and the basic portion of the moderator 231 surrounds the target T, so that the neutrons generated by the target T may be effectively moderated in all directions, so that the neutron flux and beam quality may be further improved. The lead plate 246 is disposed between the magnesium fluoride block 245 and the second transverse plate 224. The lead plate 246 is provided as the photon shield, and lead may absorb gamma rays released from the moderator. A thickness of the lead plate 246 in the direction of the neutron beam N is less than or equal to 5 cm, so that neutrons passing through the moderator are not reflected. It may be understood that, there may be alternatively another arrangement. For example, the magnesium fluoride block 245 does not contain Li-6, but a separate thermal neutron absorber composed of Li-6 is disposed between the magnesium fluoride block 245 and the second transverse plate 224, and the lead plate may be alternatively omitted.

It may be understood that, in this embodiment, PE used for the neutron shield may be replaced with another neutron shielding material; lead used for the photon shield may be replaced with another photon shielding material; lead used for the reflector may be replaced with another material with high neutron reflection capability; magnesium fluoride used for the basic portion of the moderator may be replaced with another material having a large cross section for interacting with fast neutrons and a small cross section for interacting with epithermal neutrons; Li-6 used for the thermal neutron absorber may be replaced with another material having a large cross section for interacting with thermal neutrons; the aluminum alloy used for the first supplementary unit of the moderator may be replaced with a material including at least one of Zn, Mg, Al, Pb, Ti, La, Zr, Bi, Si, and C, and an easily available material is selected, so that manufacturing costs of the moderator may be reduced, particular neutron moderation is implemented, and the beam quality is not significantly affected; and Teflon used for the second supplementary unit of the moderator may be replaced with graphite and others, and A material with a better fast neutron absorption effect than the material of the first supplementary unit is selected for the second supplementary unit, so that the content of fast neutrons in the beam may be reduced. It may be understood that at least two of the first supplementary unit, the second supplementary unit, and the basic portion of the moderator may be alternatively made of the same material.

Figure 7:
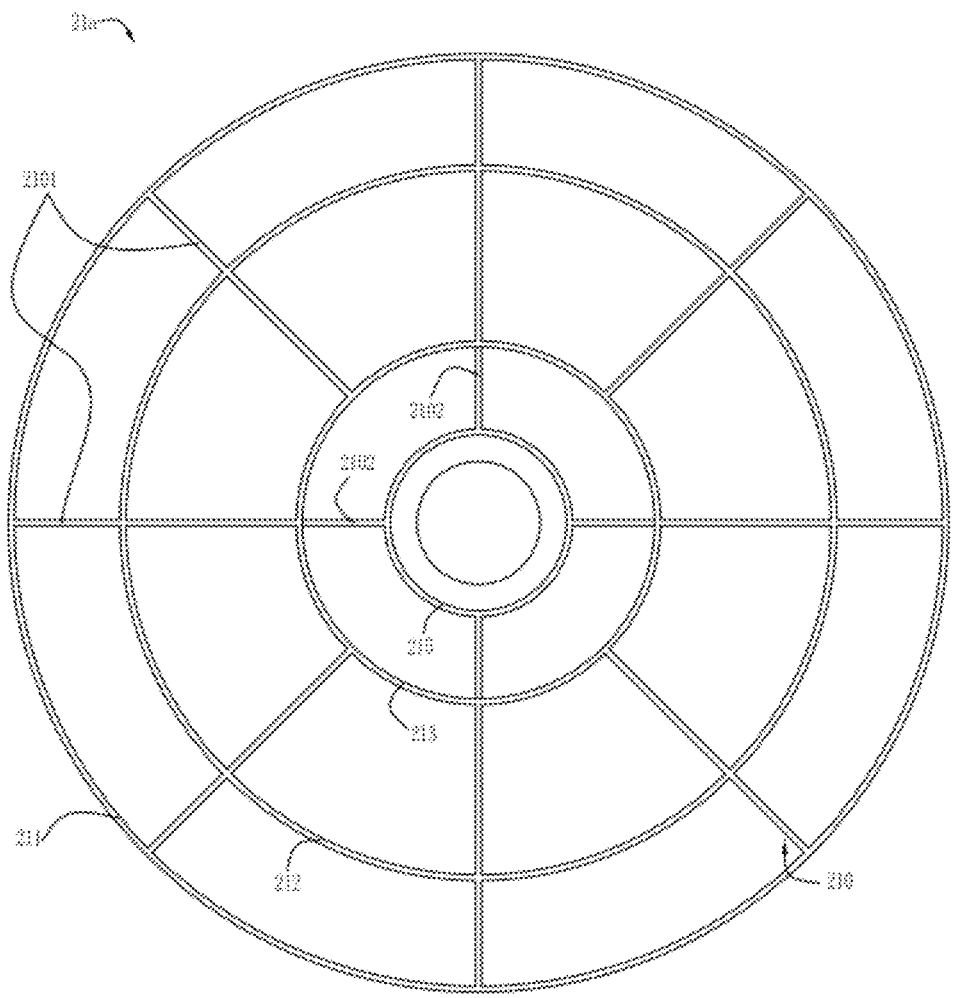
FIG. 7 is a schematic diagram of a main frame in FIG. 5 as viewed from a direction of a neutron beam N.
Figure 8:
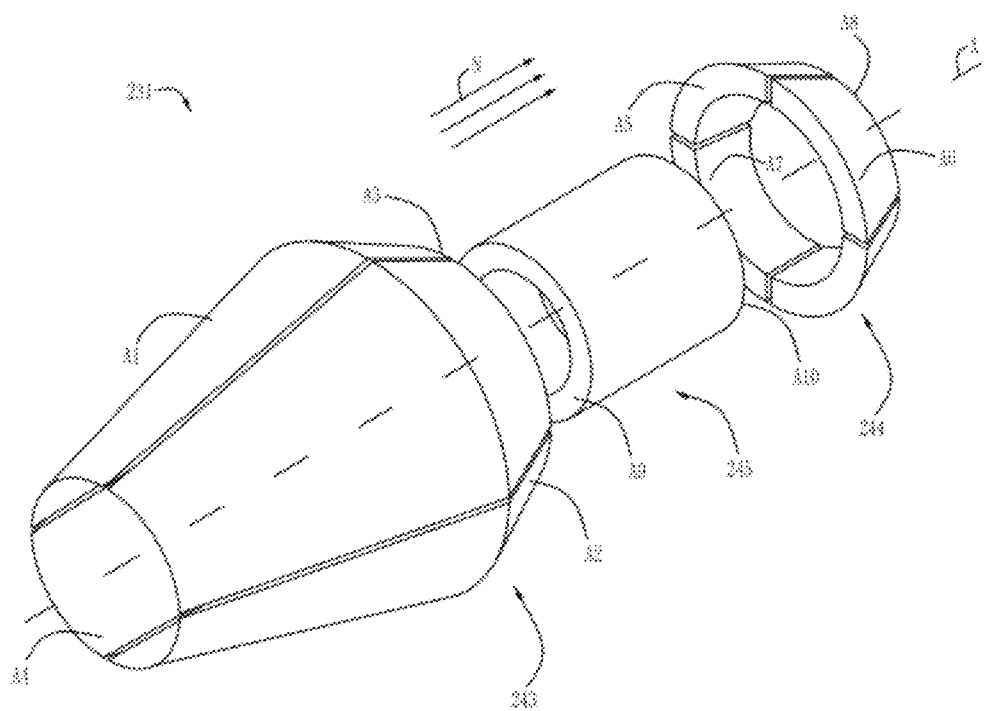
FIG. 8 is a schematic diagram of the main frame in FIG. 5 as viewed from a direction opposite to the direction of the neutron beam N.

Referring to FIG. 7 and FIG. 8, the support part 21 is further provided with radial partitions 210, a plane where the radial partition 210 is located extends through the main axis X, and each of the accommodating units C1 to C3 is circumferentially divided into at least two subregions, so that the PE block, the lead block, the aluminum alloy block, and the graphite block disposed in each of the accommodating units C1 to C3 are circumferentially equally divided into at least two submodules. In this embodiment, a first radial partition 2101 is disposed between the first side plate 221 and the second side plate, and extends from the outer wall 211 to the second inner wall 213; and a second radial partition 2102 is disposed between the first side plate 221 and the second transverse plate 224, and extends from the second inner wall 213 to the third inner wall 214 or the fourth inner wall 215. In this embodiment, there are eight first radial partitions and four second radial partitions, all evenly distributed circumferentially; and the first radial partitions and the second radial partitions are flat plates, and each second radial partition and four of the first radial partitions are in the same plane. It may be understood that there may be alternatively other quantities or arrangements of the radial partition, or the radial partition may not be disposed.

In this embodiment, the radial partitions 210, the outer wall 211, the first transverse plate 223, and the first, second, third, and fourth inner walls 212-215 are integrated as a main frame 21a, and the material is an aluminum alloy with adequate mechanical properties and a short half-life of radioactive isotopes generated by the aluminum alloy after activation by neutrons. A casting process may be used, and a support mold is integrally formed. The mold is a wooden or aluminum mold, and a sand core may be red sand or resin sand. The specific process is the method commonly used in the industry. Because there are demolding slopes by casting, according to the requirements of design and beam quality, the demolding slopes need to be removed by machining. Due to the structure and casting process, the frame structure has the advantages of adequate integrity, high rigidity, and high bearing capacity. Due to the limitation of cutting tools of machining and stress concentration on right-angle sides, all corners are rounded. Alternatively, a plate may first be rolled and welded or forged into an aluminum alloy cylinder, and the cylinder is then machined for formation.

Figure 9:
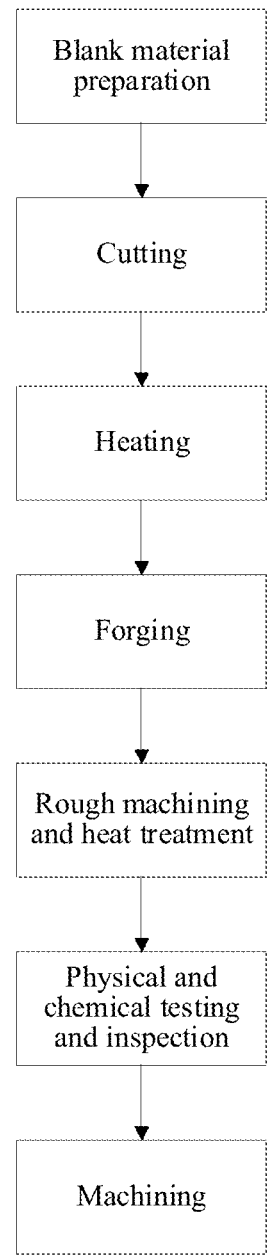
FIG. 9 is a flowchart of an embodiment of the main frame in FIG. 5 during processing.

FIG. 9 shows an embodiment of the main frame during processing. In this embodiment, the main frame 21a is a 6061 aluminum alloy, which may meet the requirements of chemical composition and mechanical properties of the material of the main frame. To meet the requirement of a short half-life of radioactive isotopes generated by the main frame after activation by neutrons, types of elements of the aluminum alloy and mass ratios of the elements should be controlled. For example, the mass percentage of Cu is ≤7%. Based on relevant calculations and experience accumulation, the chemical composition of the material of the main frame selected in this embodiment is Cu≤1.0%, Mn≤1.5%, and Zn≤1.0% (mass percentage). The chemical composition of 6061 aluminum alloy is shown in Table 1, and it may be learned from the comparison that 6061 aluminum alloy may meet the chemical composition required by the material of the main frame 21a.

tion. Nonuniform deformation reduces the plasticity of the metal, and a non-homogenized structure is obtained due to nonuniform recrystallization, so that forging properties become poor. To obtain a uniform deformed structure and optimal mechanical properties, the fewer procedures and the fewer heating times, the better. The processing of this embodiment is as follows:

1. Blank material preparation: Manufacturers such as aluminum factories treat aluminum ore into aluminum ingots, cast the aluminum ingots into a blank material, prepare the blank material into the composition of 6061 aluminum alloy that meets the national standard, and detect the blank material, for example, attached with data and experimental results in the aspects such as an alloy number, a melting furnace, a batch number, specifications, homogenization annealing, low-temperature roasting, an oxide film inspection.
2. Cutting: The blank material that meets the detection requirements is treated by using methods such as shearing, sawing, and gas cutting. For example, end surface cutting is performed, and burrs, oil stains, and sawdust are removed in time, to meet the processing requirements of forging equipment.
3. Heating: The blank material is heated before forging to reduce deformation resistance and improve plasticity. For example, a radiant resistance heating furnace is used, there is circulating air in the furnace to keep the temperature accurate and uniform, and the furnace temperature deviation may be controlled in a range of ±10° C. In this embodiment, the maximum initial forging temperature is 520° C., the final forging temperature is 450° C., and the allowable limit temperature is 530° C. It may be understood that other heating equipment may be alternatively used. The determination of a heat preservation time needs to fully consider factors such as the thermal conductivity of an alloy, blank material specifications, heat transfer modes of heating equipment, and the like. In this embodiment, the heating time is determined according to dissolution of a strengthening phase and structure homogenization. In this state, adequate plasticity may be obtained, and the forging performance of an aluminum alloy may be improved. It may be understood that the blank material

TABLE 1

| Chemical composition (%) | | | | | | | | Others | | |
|---|---|---|---|---|---|---|---|---|---|---|
| Cu | Mn | Mg | Zn | Cr | Ti | Si | Fe | Single | Total | Al |
| 0.15-0.4 | 0.15 | 0.8-1.2 | 0.25 | 0.04-0.35 | 0.15 | 0.4-0.8 | 0.7 | 0.05 | 0.15 | Allowance |

To meet the support of the main frame 21a on the main part 23 of the beam shaping assembly, the mechanical properties of the main frame need to meet the requirements. According to CAE simulation calculation and empirical adjustments, for the aluminum alloy main frame selected in this embodiment, the tensile strength is ≥150 MPa, and the yield strength is ≥100 MPa.

Because 6061 aluminum alloy is a wrought aluminum alloy, a free forging method is used in this embodiment, the structure and properties of the aluminum alloy are changed by using a plastic forming method, and raw materials may be saved. In the free forging procedure, the quality of a forging largely depends on a metal structure obtained during deformation, especially the uniformity of forging deformamay be alternatively heated before the cutting in step 2. In this case, before the blank material is heated, for example, before the blank material enters a heating furnace, it is necessary to remove oil stains, dust, and other dirt to avoid polluting air in the furnace.

4. Forging: The material of 6061 aluminum alloy is polycrystalline, there are grain boundaries between grains, and there are subgrains and phase boundaries inside the grains. Therefore, the material is subjected to plastic deformation based on the plasticity of the material by using an external force to obtain a forging with the required shape (for example, a cylinder), size, and particular structural properties. A cast structure of the metal blank material is eliminated through forging deformation, thereby greatly improving the plasticity and mechanical properties. In this embodiment, a free forging method such as upsetting and drawing is used, under the condition that the forging temperature is not less than a specified temperature, static forging is repeated according to processes of the foregoing two methods to obtain precise grains in the structure, and the forging equipment has the precision of forging a blank.

5. Rough machining and heat treatment: To finally obtain the mechanical properties that meet the requirements of use, it is also necessary to change the structure and properties of the metal material through heat treatment to change the internal quality of the metal. In this embodiment, a cylinder is obtained by forging in step 4. When heat treatment is directly performed on the cylinder, it is difficult to ensure the performance of a material at the center of the cylinder. Therefore, a hole is drilled at a center position (that is, the regions of the cylinder corresponding to the fourth accommodating unit C4) of the forged cylinder through rough machining, and deep heat treatment is then performed, so that it may be ensured that the main frame is close to the center position (to form a main frame portion of the fourth accommodating unit C4) and ensure the overall material properties after the heat treatment. In addition, the fourth accommodating unit C4 accommodates the basic portion of the moderator, so that the support for the moderator may be ensured, and the moderator is prevented from deformation and damage, to avoid affecting the target change and beam quality. It may be understood that the rough machining further includes preliminary machining of hollow regions (that is, regions of the cylinder corresponding to the first accommodating unit C1, the second accommodating unit C2, and the third accommodating unit C3) between the outer wall 211 and the inner walls 212-215 of the main frame, for example, a solid portion of the cylinder obtained by forging in the regions is drilled and milled. In this embodiment, the rough machining is not performed in the regions, to prevent the regions from easy deformation caused by a thin thickness during heat treatment after the rough machining. In the case that the process may ensure the material properties of a center region and other regions, the rough machining may not be performed. The rough machining should leave an allowance for subsequent machining.

The heat treatment used in this embodiment is T6 (solid solution+aging). Solution treatment is a precedent procedure for precipitation hardening of an alloy. A solid solution formed during the solution treatment is rapidly cooled to obtain a metastable supersaturated solid solution, which creates conditions for natural aging and artificial aging, and significantly improves the strength and hardness. Aging treatment is required after the solution treatment, aluminum after solution treatment is kept at a particular temperature for a particular time, and a supersaturated solid solution decomposes to cause the strength and hardness of the alloy to increase greatly, and aluminum may be kept at room temperature or heated. The aging treatment is the last procedure of the heat treatment, which may improve and determine the final mechanical properties of the aluminum alloy. The heating temperature and the heat preservation time may be selected according to an actual situation. It may be understood that other heat treatment processes may be alternatively used, as long as the mechanical properties that meet the requirements of use may be met.

6. Physical and chemical testing and inspection: After the heat treatment, physical and chemical testing and inspection need to be performed, including size testing, element testing, mechanical property testing, non-destructive ultrasonic flaw detection testing, and the like. The testing may be performed after the heat treatment by relevant personnel of the heat treatment, or the inspection may be performed before machining by relevant personnel of the machining (see below). The mechanical property testing may be performed by cutting part of the material in a relevant region of a workpiece after the heat treatment. In this embodiment, the part removed by drilling a hole at the center position may be subjected to the heat treatment during the rough machining, and the part is tested to approximately represent the properties of the inner walls 214 and 215 close to the main axis X; and the region between the outer wall 211 and the inner walls 212-215 is tested by cutting the material of the forged cylinder after heat treatment in this region. It may be understood that, when the rough machining is performed on the hollow regions between the outer wall 211 and the inner walls 212-215, the part cut off by performing rough machining on the region is tested after heat treatment to approximately represent the properties of the region, and the selection of the region may be marked on a drawing. The foregoing region is sampled for mechanical testing to obtain the yield strength and tensile strength. The non-destructive testing uses ultrasonic flaw detection, which may be comprehensive inspection or partition inspection. In this embodiment, the ultrasonic flaw detection testing is performed on the inner wall close to the center.

7. Machining: After testing and inspection, and a forged body after the heat treatment meets the requirements, machining is performed to obtain the main frame with a final required shape and size. It may be understood that the machining may include conventional machining methods such as drilling, milling, and turning. In this embodiment, a large gantry milling machine is used for milling, and cooperates with programming software for automatic processing.

The main frame 21a and the second transverse plate 224 are connected by a bolt. A first threaded hole is uniformly machined in an end surface, facing the second side plate 222, of the fourth inner wall 215. A first through hole is uniformly machined at a position, corresponding to the first threaded hole, in the second transverse plate 224. The bolt passes through the first through hole to be connected to the first threaded hole. Due to the assembly of the bolt, the hole diameter of the first through hole is slightly greater than the hole diameter of the first threaded hole, and the quantities of the first threaded holes and the first through holes only need to meet the connection strength. The material of the first side plate 221, the second side plate 222, and the second transverse plate 224 is a lead-antimony alloy. Lead may further shield against radiation, and the lead-antimony alloy has a relatively high strength. The outer contours of the first side plate 221 and the second side plate 222 are consistent with the outer contour of the outer wall 211. The first side plate 221, the second side plate 222, and the second transverse plate 224 are connected to the main frame by bolts. Second threaded holes are uniformly machined respectively in end surfaces, facing the first side plate, the second side plate, and the second transverse plate, of the inner wall of the main frame 21a. Second through holes are uniformly machined at positions, corresponding to the second threaded holes, of the first side plate 221, the second side plate 222, and the second transverse plate 224. Due to the assembly of the bolts, the hole diameter of the second through hole is slightly greater than the hole diameter of the second threaded hole, and the quantities of the second threaded holes and the second through holes only need to meet the connection strength.

It may be understood that, in this embodiment, the materials of the main frame, the side plate, and the end plate (the second transverse plate) only need to have a particular strength and a short half-life of radioactive isotopes generated by the materials after activation by neutrons (for example, less than 7 days), and the material properties of the main frame may meet the requirements of supporting the beam shaping assembly, such as an aluminum alloy, a titanium alloy, a lead-antimony alloy, cobalt-free steel, carbon fiber, PEEK, or a high polymer. Other detachable connections or non-detachable connections may be provided between the side plate, the end plate (the second transverse plate), and the main frame. When the detachable connection is used, it is convenient to replace each portion of the main part. In this embodiment, the support part and the main part filled within the support part of the beam shaping assembly may alternatively have another construction manner.

During construction, the main frame 21a is first put into a mounting hole reserved by the support part of the beam shaping assembly, and the outer wall 211 of the main frame 21a and the support part of the beam shaping assembly are connected by bolts. Filling of the main part and mounting of the first side plate, the second side plate, and the second transverse plate are then performed. Due to low density of PE, aluminum alloy, and graphite, the corresponding regions may be filled entirely. Because lead is relatively heavy, lead may be manually filled in pieces in the direction of the neutron beam N or may be entirely filled with a machine. Magnesium fluoride may also be filled entirely or in pieces. After the beam shaping assembly is mounted, the transmitting tube, the target, the collimator, and other components are mounted. The collimator 30 is disposed at a rear portion of the beam exit. The epithermal neutron beam from the collimator 30 is irradiated to the patient 200, and is moderated to be thermal neutrons after passing through superficial normal tissues to reach a tumor cell M. In this embodiment, the collimator is fixed to the main frame 21a by bolts, a third threaded hole is reserved in an end surface, facing the second side plate, of the second inner wall 213, and a third through hole is uniformly machined at a position, corresponding to the third threaded hole, of the second side plate 222. Due to the assembly of the bolt, the hole diameter of the third through hole is slightly greater than the hole diameter of the third threaded hole, and the quantities of the third threaded holes and the third through holes only need to meet the connection strength. It may be understood that the collimator 30 may be alternatively fixed in another connection manner, the collimator 30 may be alternatively removed or replaced with another structure, and the neutron beam from the beam exit directly irradiates the patient 200. In this embodiment, a radiation shielding device 50 is further disposed between the patient 200 and the beam exit to shield normal tissue of the irradiated subject from irradiation by the beam from the beam exit. It should be understood that the radiation shielding device 50 may not be disposed.

The term 'cylindrical' or 'cylindrical section' referred in the embodiment of the present disclosure is an element with the contour in a substantially unchanged trend from one side to the other side along the illustrated direction. One of contour lines may be a line segment, like a corresponding one of the cylinder, or may be a high-curvature arc approximate to the line segment, like a corresponding one of a sphere with high curvature. The integral surface of the contour may be continuously connected or not if the surface of the cylinder or the high-curvature sphere is provided with many protrusions and grooves.

The term 'tapered' or 'tapered section' referred in the embodiment of the present disclosure is an element with the contour in a tapering trend from one to the other side along the illustrated direction. One of contour lines may be a line segment, like a corresponding one of the cone, or may be an arc, like a corresponding one of the sphere, and the integral surface of the contour may be continuously connected or not if the surface of the cone shape or the spherical shape is provided with plenty of protrusions and grooves.

Although the illustrative embodiments of the present invention have been described above in order to enable those skilled in the art to understand the present invention, it should be understood that the present invention is not to be limited the scope of the embodiments. For those skilled in the art, as long as various changes are within the spirit and scope as defined in the present invention and the appended claims, these changes are obvious and within the scope of protection claimed by the present invention.

What is claimed is:

1. A beam shaping assembly for a neutron capture therapy system, wherein the neutron capture therapy system includes a neutron generating device, neutrons generated by the neutron generating device form a neutron beam, the neutron beam defines a main axis, the beam shaping assembly is configured to adjust beam quality of the neutron beam, and the beam shaping assembly includes:
   a support part and a main part filled within the support part, wherein the support part includes a support frame, the support frame is formed by heating a blank material with a heating equipment and then performing forging into a cylinder with a forging equipment, and the cylinder is processed with a machining equipment after rough machining and heat treatment.

2. The beam shaping assembly according to claim 1, wherein a material of the support frame is an aluminum alloy, the mass percentage of Cu in the aluminum alloy is ≤7%, the tensile strength of the material is ≥150 MPa, and the yield strength of the material is ≥100 MPa.

3. The beam shaping assembly according to claim 2, wherein the aluminum alloy is a wrought aluminum alloy, the forging equipment is free forging equipment, and the free forging equipment includes upsetting and drawing equipment.

4. The beam shaping assembly according to claim 1, wherein the heating equipment is a radiant resistance heating furnace, there is circulating air in the furnace to keep the temperature accurate and uniform, the furnace temperature deviation is ±10° C., the maximum initial forging temperature is 520° C., the final forging temperature is 450° C., and the allowable limit temperature is 530° C.

5. The beam shaping assembly according to claim 1, wherein the main part includes a moderator, a reflector, and a radiation shield, the moderator slows down neutrons generated by the neutron generating device to an epithermal neutron energy range, the reflector surrounds the moderator and guides neutrons that deviate from the main axis back to the main axis to increase the intensity of an epithermal neutron beam, the radiation shield is provided to shield against leaked neutrons and photons to reduce the dose to normal tissues in a non-irradiation area, the support frame forms at least one accommodating unit, and at least one of the accommodating units accommodates at least a part of the main part.

6. The beam shaping assembly according to claim 5, wherein the accommodating unit includes a first accommodating unit accommodating at least a part of the moderator, the first accommodating unit is located at the center of the support frame in the radial direction, and the rough machining is drilling holes in regions of the cylinder corresponding to the first accommodating unit.

7. The beam shaping assembly according to claim 6, wherein the accommodating unit includes a second accommodating unit accommodating at least one of the moderator, the reflector, and the radiation shield, the support frame includes an outer wall circumferentially closed around the main axis and at least one inner wall, the second accommodating unit is formed between the outer wall and the inner wall or between the inner walls, and the rough machining further includes preliminary machining of regions of the cylinder corresponding to the second accommodating unit.

8. The beam shaping assembly according to claim 1, wherein the heat treatment includes solution treatment and aging treatment.

9. A method for treating a support frame of a beam shaping assembly, including:
heating: heating a blank material that meets the material requirements of the support frame at a particular temperature and for a particular time;
forging: forging the heated blank material into a cylinder;
rough machining: drilling a hole is at a center position of the cylinder obtained by forging;
heat treatment: performing heat treatment on a forged body obtained after the rough machining; and
machining: machining the forged body after the heat treatment to obtain the support frame with a final required shape and size.

10. The method for treating a support frame of a beam shaping assembly according to claim 9, wherein:
before the step of the heating, the blank material is detected to meet the raw material requirements of the support frame;
before the step of the forging, the blank material is treated to meet the processing requirements of the forging equipment;
the forging is free forging, including upsetting and drawing;
the heat treatment includes solution treatment and aging treatment; and
after the heat treatment, physical and chemical testing and inspection are performed, including size testing, element testing, mechanical property testing, and non-destructive ultrasonic flaw detection testing.

* * * * *